United States Patent
Choi et al.

(10) Patent No.: US 11,583,264 B2
(45) Date of Patent: Feb. 21, 2023

(54) APPARATUS FOR CLOSED REDUCTION OF BONE FRACTURE

(71) Applicants: THE ASAN FOUNDATION, Seoul (KR); UNIVERSITY OF ULSAN FOUNDATION FOR INDUSTRY COOPERATION, Ulsan (KR)

(72) Inventors: Jae Soon Choi, Seoul (KR); Young Jin Moon, Seoul (KR); Jong Woo Choi, Seoul (KR); Woo Shik Jeong, Seoul (KR); Ho Yul Lee, Paju-si (KR)

(73) Assignees: THE ASAN FOUNDATION, Seoul (KR); UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 595 days.

(21) Appl. No.: 16/597,046

(22) Filed: Oct. 9, 2019

(65) Prior Publication Data

US 2020/0038063 A1     Feb. 6, 2020

Related U.S. Application Data

(63) Continuation of application No. PCT/KR2018/002765, filed on Mar. 8, 2018.

(30) Foreign Application Priority Data

Apr. 10, 2017  (KR) .......................... 10-2017-0046241

(51) Int. Cl.
*A61B 17/02*     (2006.01)
*A61B 17/17*     (2006.01)
(Continued)

(52) U.S. Cl.
CPC ...... *A61B 17/0218* (2013.01); *A61B 17/1721* (2013.01); *A61B 17/66* (2013.01);
(Continued)

(58) Field of Classification Search
CPC .......... A61B 90/14; A61B 90/17; A61B 5/708; A61B 2017/00796; A61B 17/0206; A61B 17/0208; A61B 17/0293; A61B 17/0218
See application file for complete search history.

(56) References Cited

U.S. PATENT DOCUMENTS 2,291,413 A      7/1942   Siebrandt
6,152,874 A  *  11/2000   Looney .............. A61B 17/0206
                                                   600/222
(Continued)

FOREIGN PATENT DOCUMENTS

CN     2652342 Y    11/2004
EP     3545884 A2   10/2019
(Continued)

OTHER PUBLICATIONS

International Search Report issued in PCT/KR2018/002765; dated Jun. 15, 2018.
(Continued)

*Primary Examiner* — Julianna N Harvey
(74) *Attorney, Agent, or Firm* — Studebaker & Brackett PC

(57) ABSTRACT

The present disclosure relates to an apparatus for closed reduction of a bone fracture. The apparatus includes at least: a pulling adaptor including: a handle configured to be gripped by an operator; an insertion rod that is extended from the handle in a longitudinal direction of the handle, and configured to be inserted into the bone fracture which is depressed in at least one area thereof; and a pulling lug that is bent and extended from an end of the insertion rod such that a longitudinal direction of the pulling lug is perpendicular to a longitudinal direction of the insertion rod or such that the pulling lug is inclined with respect to the insertion rod, the pulling lug being configured to be inserted into the (Continued)

at least one depressed area of the bone fracture, in order to pull the bone fracture.

5 Claims, 20 Drawing Sheets

(51) Int. Cl.
    *A61B 17/66*     (2006.01)
    *A61B 17/80*     (2006.01)
    *A61B 17/00*     (2006.01)
    *A61B 17/56*     (2006.01)

(52) U.S. Cl.
    CPC ...... *A61B 17/8057* (2013.01); *A61B 17/8061* (2013.01); *A61B 2017/00792* (2013.01); *A61B 2017/564* (2013.01)

(56) References Cited

U.S. PATENT DOCUMENTS

| | | | | |
|---|---|---|---|---|
| 6,464,634 B1* | 10/2002 | Fraser | ................ | A61B 17/0293 |
| | | | | 600/233 |
| 6,692,502 B1 | 2/2004 | Ertl et al. | | |
| 6,824,511 B1* | 11/2004 | Bell | ....................... | A61B 17/02 |
| | | | | 600/227 |
| 2002/0115909 A1* | 8/2002 | Bolser | .............. | A61B 17/00008 |
| | | | | 600/210 |
| 2009/0281578 A1 | 11/2009 | Spencer | | |
| 2014/0350613 A1 | 11/2014 | Pascual | | |
| 2022/0071614 A1* | 3/2022 | Bertoli | ................... | A61B 17/02 |

FOREIGN PATENT DOCUMENTS

| | | |
|---|---|---|
| GB | 1203716 A | 9/1970 |
| JP | 2003-519527 A | 6/2003 |
| KR | 10-0536168 B1 | 12/2005 |
| KR | 10-2013-0011347 A | 1/2013 |
| KR | 10-2014-0119313 A | 10/2014 |
| WO | 02/096294 A2 | 12/2002 |

OTHER PUBLICATIONS

"Breast Plastic Surgery Instrument/Rechardson East Retractor/U.S. Army Retractor/Army Retractor, Rechardson Retractor/Coating Retractor"; S Medical; Jun. 15, 2016; URL: http://blog.naver.com/psclinic0817/220736882620.

The extended European search report issued by the European Patent Office dated Apr. 9, 2020, which corresponds to European Patent Application No. 18783647.3-1122 and is related to U.S. Appl. No. 16/597,046.

* cited by examiner

APPARATUS FOR CLOSED REDUCTION OF BONE FRACTURE

CROSS-REFERENCE TO RELATED APPLICATIONS

The present application is a continuation of International Patent Application No. PCT/KR2018/002765, filed Mar. 8, 2018, which is based upon and claims the benefit of priority to Korean Patent Application No. 10-2017-0046241, filed on Apr. 10, 2017. The disclosures of the above-listed applications are hereby incorporated by reference herein in their entirety.

BACKGROUND

Embodiments of the inventive concept described herein relate to an apparatus for the closed reduction of a bone fracture, and more particularly, to an apparatus for the closed reduction of a bone fracture, capable of recovering a depressed bone by pulling the depressed bone.

In general, a plastic surgery has been performed with respect to patients having facial bones depressed due to external impacts.

According to such a plastic surgery, a hard surgical instrument is inserted into the depressed area or an area formed by partially cutting the depressed area to perform an operation of spreading or pulling in a lever principle.

For example, when the hard instrument provided in a linear form is inserted into the depressed bone and pulled, other surrounding bones may be damaged.

In addition, the direction of force for pulling out a bone differs from, that is, is inclined with respect to a direction of force of the surgical instrument, so it is difficult to smoothly transmit the force.

Accordingly, in most of cases, since other bones may be damaged in the operation, a skin may be cut and operated to recover the damaged bones.

Although the necessity for such a surgery instrument is increased as the minimally invasive surgery has been increasingly required to minimize a scar, the development of the relevant instrument is not made much more than expected.

According to a conventional surgery instrument, for example, when a frontal sinus fracture occurs, and when there are present several fracture fragments, even if the fracture fragment formed in one direction is reduced (recovered), a fracture fragment formed at a remaining lever part may be more severed in parallagma.

Accordingly, there is required the development of a surgery instrument capable of being inserted into a smaller incision, pulling a fracture fragment in a vertical direction without applying force to the fracture fragment in an opposite direction, or simultaneously pulling a plurality of fracture fragments.

SUMMARY

Embodiments of the inventive concept provide an apparatus for the closed reduction of a bone fracture, which can easily perform insertion and removal of the apparatus through a smaller incision, and can recover a depressed fracture by stably pulling the depressed fracture regardless of a skin thickness.

Embodiments of the inventive concept provide an apparatus for the closed reduction of a bone fracture, which can be mounted at various parts and used by changing the pulling direction and can be minimized in fluctuation when the operator pulls the fracture fragment, thereby stably recovering the fracture fragment.

Embodiments of the inventive concept provide an apparatus for the closed reduction of a bone fracture, which can recover a depressed fracture by pulling the depressed fracture while precisely and finely adjusting the depressed fracture.

According to some embodiments, an apparatus for closed reduction of a bone fracture includes: a pulling adaptor including: a handle configured to be gripped by an operator; an insertion rod that is extended from the handle in a longitudinal direction of the handle, and configured to be inserted into the bone fracture which is depressed in at least one area thereof; and a pulling lug that is bent and extended from an end of the insertion rod such that a longitudinal direction of the pulling lug is perpendicular to a longitudinal direction of the insertion rod or such that the pulling lug is inclined with respect to the insertion rod, the pulling lug being configured to be inserted into the at least one depressed area of the bone fracture, in order to pull the bone fracture.

BRIEF DESCRIPTION OF DRAWINGS

The above and other objects and features will become apparent from the following description with reference to the following figures, wherein like reference numerals refer to like parts throughout the various figures unless otherwise specified, and wherein.

DETAILED DESCRIPTION

Figure 1:
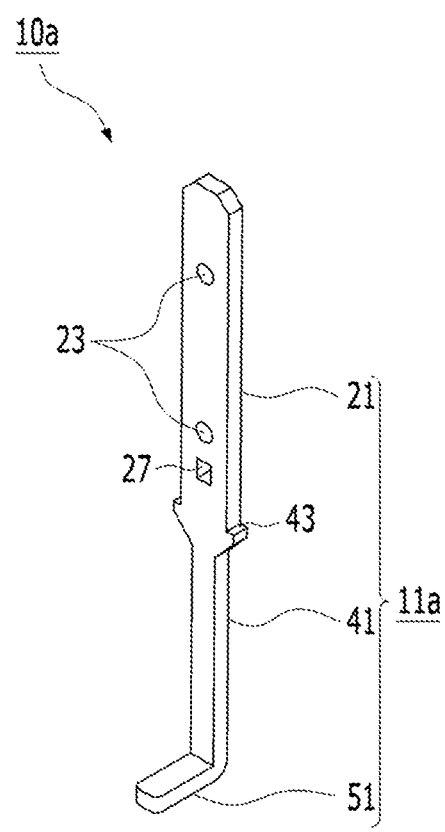
FIG. 1 is a view illustrating an apparatus for a closed reduction of a bone fracture, according to a first embodiment.

Advantage points and features of the inventive concept and a method of accomplishing thereof will become apparent from the following description with reference to the following figures, wherein embodiments will be described in detail with reference to the accompanying drawings. The inventive concept, however, may be embodied in various different forms, and should not be construed as being limited only to the illustrated embodiments. Rather, these embodiments are provided as examples so that this disclosure will be thorough and complete, and will fully convey the concept of the inventive concept to those skilled in the art. The inventive concept may be defined by scope of the claims. Meanwhile, the terminology used herein to describe embodiments of the inventive concept is not intended to limit the scope of the inventive concept.

The terminology used in the inventive concept is provided for the illustrative purpose, but the inventive concept is not limited thereto. As used herein, the singular terms "a," "an" and "the" are intended to include the plural forms as well, unless the context clearly indicates otherwise. Furthermore, it will be further understood that the terms "comprises", "comprising," "includes" and/or "including", when used herein, specify the presence of stated elements, steps, operations, and/or devices, but do not preclude the presence or addition of one or more other components, steps, operations and/or devices. The same reference numerals will be assigned to the same component throughout the whole specification, and "and/or" refers to that components described include not only individual components, but at least one combination of the components. Unless otherwise defined, all terms (including technical and scientific terms) used herein have the same meaning as commonly understood by those skilled in the art. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, embodiments will be described with reference to accompanying drawings.

Before description, according to various embodiments, the same reference numeral will be assigned to the same component, and the first embodiment will be representatively described. According to another embodiment, the following description will be made while focusing on the difference between the first embodiment and other embodiments.

It should be noticed that an apparatus for the closed reduction of a bone fracture according to embodiments is applied to various bones as well as a facial bone, and that, in some embodiments, the closed reduction is a closed manual reduction.

FIG. 1 is a view illustrating an apparatus for the closed reduction of a bone fracture, according to a first embodiment. According to the first embodiment, an apparatus 10a for the closed reduction of a bone fracture is used independently, or used in combination with a hand piece on which a pulling adaptor 11a of the apparatus 10a is mounted. The hand piece is described later.

As illustrated in FIG. 1, according to the first embodiment, the pulling adaptor 11a of the apparatus 10a for the closed reduction of the bone fracture includes a handle 21, an insertion rod 41, and a pulling lug 51.

The handle 21 has a form of a bar having a predetermined length such that an operator grips the handle 21. According to the first embodiment, the handle 21 includes a pair of coupling holes 23 and a pin hole 27 that penetrates the handle 21 such that the apparatus 10a for the closed reduction of the bone fracture is mounted on the hand piece and used. In this case, although the handle 21 includes the pair of coupling holes 23 and the pin hole 27 that penetrates the handle 21 according to the present embodiment, the inventive concept is not limited thereto. In different cases, for example, the apparatus 10a for the closed reduction of the bone fracture according to the first embodiment may be used independently without being mounted on the hand piece as the pair of coupling holes 23 and the pin hole 27 are not formed in the handle 21.

The insertion rod 41 has the form of a bar and extends in the lengthwise direction from the handle 21. At least a partial area of the insertion rod 41 is inserted into the depressed fracture 1 (see e.g., FIG. 16A). The insertion rod 41 has a sectional surface smaller than the handle 21 and an incision 3 such that the insertion rod 41 is inserted into the smaller incision 3 (see e.g., FIG. 16A) of a fracture 1 which is depressed.

In addition, stoppers 43 are formed at the boundary area between the insertion rod 41 and the handle 21. The stoppers 43 protrude along both edges of the insertion rod 41 to be inclined with respect to an axis of the handle 21 toward the handle 21. Accordingly, when the apparatus 10a for the closed reduction of the bone fracture according to the first embodiment is mounted on the hand piece as described later and then being used, the movement of the apparatus 10a for the closed reduction of a bone fracture according of the first embodiment toward the hand piece is limited by the stopper 43.

The pulling lug 51 is bent from an end of the insertion rod 41 while extending perpendicularly to the insertion rod 41. The pulling lug 51 is inserted into the fracture 1 to pull the fracture 1. In some embodiments, the end of the insertion rod 41 is a free end. The bending part between the pulling lug 51 and the insertion rod 41 is preferably rounded with the predetermined radius of a curvature such that the bending part is easily inserted into the incision 3 of the fracture 1.

Although the present embodiment is illustrated in that the pulling lug 51 is bent perpendicularly to the insertion rod 41 while extending, the inventive concept is not limited. In different cases, for example, the pulling lug 51 may extend while being bent downward or upward, corresponding to the bend of the fracture 1 which is depressed.

Regarding the apparatus 10a for the closed reduction of the bone fracture according to the first embodiment, the apparatus 10a for the closed reduction of the bone fracture may be inserted in the incision 3 of the depressed fracture 1 while being inclined, may be easily inserted into the incision 3 and easily remove the fracture 1 when there is present a space inside the fracture 1, or may recover the fracture 1 by stably pulling the depressed fracture 1 regardless of the thickness of a skin.

Figure 2:
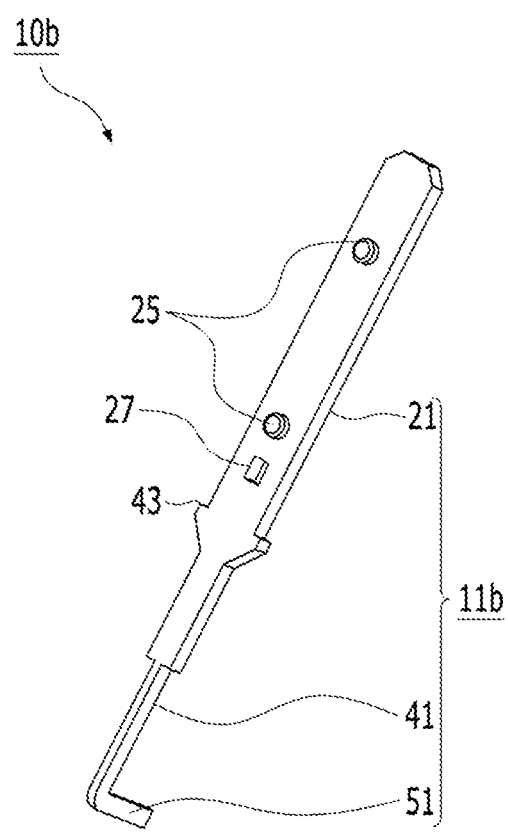
FIG. 2 is a view illustrating an apparatus for a closed reduction of a bone fracture, according to a second embodiment.

FIG. 2 is a view illustrating an apparatus for the closed reduction of a bone fracture, according to a second embodiment. According to a second embodiment, an apparatus 10b for the closed reduction of a bone fracture is used independently, or used in combination with the hand piece on which a pulling adaptor 11b of the apparatus 10b is mounted.

As illustrated in FIG. 2, according to the second embodiment, the apparatus 10b for the closed reduction of the bone fracture has coupling protrusions 25 protruding on the handle 21 instead of the coupling holes such that the apparatus 10b for the closed reduction of the bone fracture according to the second embodiment is mounted and used, differently from the first embodiment.

In this case, although the handle 21 includes the pair of coupling protrusions 25 formed on the handle 21 and the pin hole 27 that penetrates the handle 21 according to the present embodiment, the inventive concept is not limited thereto. In different cases, for example, the apparatus 10b for the closed reduction of the bone fracture according to the second embodiment may be used independently without being mounted on the hand piece as the pair of coupling protrusions 25 are not formed.

Regarding the apparatus 10a for the closed reduction of the bone fracture according to the first embodiment and the apparatus 10b for the closed reduction of a bone fracture according to the second embodiment, the apparatus 10a or the apparatus 10b may be inserted in the incision 3 of the depressed fracture 1 while being inclined, may be easily inserted into the incision 3 and easily remove the fracture 1 when there is present a space inside the fracture 1, or may recover the fracture 1 by stably pulling the depressed fracture 1 regardless of the thickness of a skin.

Figure 3A:
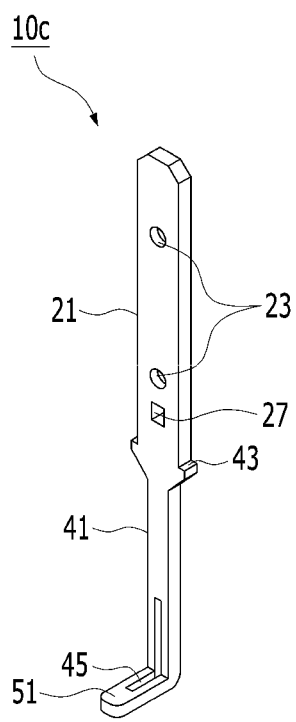
FIGS. 3A and 3B illustrate an apparatus for a closed reduction of a bone fracture, according to a third embodiment.
Figure 3B:
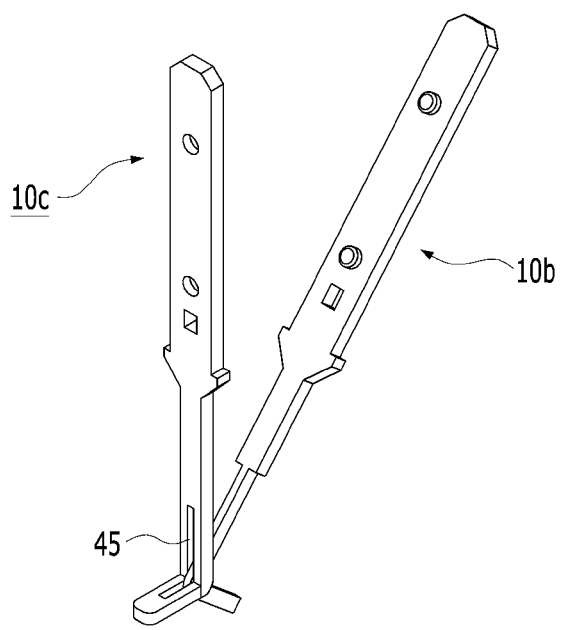

FIGS. 3A and 3B illustrate an apparatus for the closed reduction of a bone fracture, according to a third embodiment. According to the third embodiment, an apparatus 10c for the closed reduction of the bone fracture is used independently, or used in combination with a hand piece on which a pulling adaptor is mounted.

FIGS. 3A and 3B illustrate an apparatus for the closed reduction of a bone fracture, according to a third embodiment. According to the third embodiment, an apparatus 10c for the closed reduction of the bone fracture is used independently or, used in combination with a hand piece on which a pulling adaptor of the apparatus 10c is mounted. As illustrated in FIG. 3A, according to the third embodiment, the apparatus 10c for the closed reduction of the bone fracture further includes a slot 45 that penetrates a portion of the insertion rod 41 and a portion of the pulling lug 51, differently from the first embodiment to be described above.

The slot 45 has a predetermined length in a lengthwise direction of the insertion rod 41 and the pulling lug 51.

Meanwhile, according to the third embodiment, although the apparatus 10c for the closed reduction of the bone fracture is independently used, the apparatus 10c may be used together with the apparatus 10b for the closed reduction of the bone fracture according to the second embodiment.

For example, when the depressed fracture 1 having the incision 3 in a smaller size is operated to be recovered, the apparatus 10b for the closed reduction of a bone fracture according to the second embodiment is easily inserted into the incision 3 and used, in the state of being partially inserted into the apparatus 10c for the closed reduction of a bone fracture according to the third embodiment as illustrated in FIG. 3B.

Figure 4:
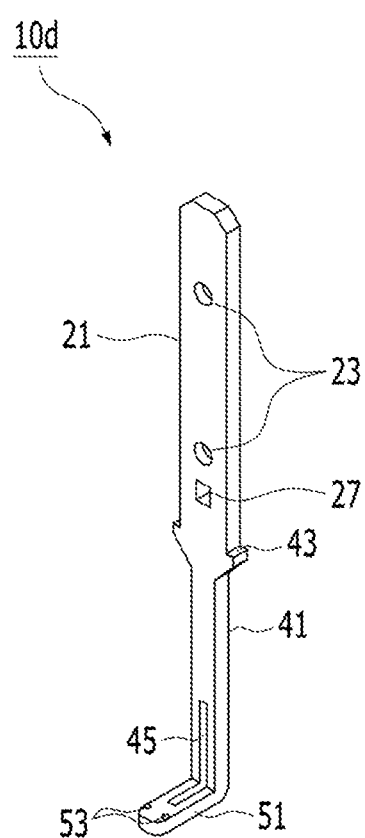
FIG. 4 is a view illustrating an apparatus for a closed reduction of a bone fracture, according to a fourth embodiment.

Although not illustrated, the apparatus 10c for the closed reduction of the bone fracture according to the third embodiment may be used together with the apparatus 10a for the closed reduction of the bone fracture according to the first embodiment. FIG. 4 is a view illustrating an apparatus for the closed reduction of a bone fracture, according to a fourth embodiment. According to the fourth embodiment, an apparatus 10d for the closed reduction of the bone fracture is used independently or, used in combination with a hand piece on which a pulling adaptor of the apparatus 10c is mounted. As illustrated in FIG. 4, according to the fourth embodiment, the apparatus 10d for the closed reduction of the bone fracture according to the fourth embodiment further includes at least one anti-slip protrusion that protrudes from an upper surface of the pulling lug, which is different from the third embodiment described above. The at least one anti-slip protrusion is configured to prevent the bone fracture from being slipped over the pulling lug. In some embodiments, the at least one anti-slip protrusion is a pair of anti-slip protrusions 53 as shown in FIG. 4.

The anti-slip protrusion 53 has a semi-spherical sectional surface form and protrudes on one surface, which is toward the fracture 1, of the pulling lug 51. The anti-slip protrusion 53 prevents the fracture 1 from being slipped over the pulling lug 51 when the pulling lug 51 pulls the fracture 1. In this case, one or three anti-slip protrusions 53 may be provided.

Regarding the apparatus 10d for the closed reduction of a bone fracture according to the fourth embodiment, the frictional force between the pulling lug 51 and the fracture 1 is increased due to the anti-slip protrusions 53 when the depressed fracture 1 is pulled, thereby preventing the pulling lug 51 from being slip out of the fracture 1. Accordingly, the depressed fracture 1 may be stably pulled and recovered regardless of the thickness of the skin.

Figure 5:
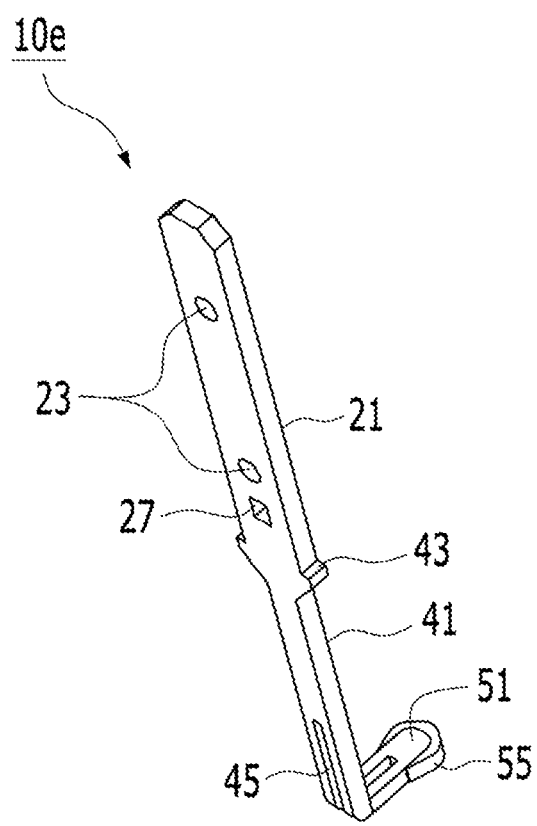
FIG. 5 is a view illustrating an apparatus for a closed reduction of a bone fracture, according to a fifth embodiment.

FIG. 5 is a view illustrating an apparatus for the closed reduction of a bone fracture, according to a fifth embodiment. According to the fifth embodiment, an apparatus 10e for the closed reduction of a bone fracture is used independently, or used in combination with a hand piece on which a pulling adaptor of the apparatus 10e is mounted.

As illustrated in drawings, according to the fifth embodiment, the apparatus 10e for the closed reduction of the bone fracture further includes a support 55, which is different from the third embodiment.

The support 55 is extended to be protruded from an end portion of the pulling lug 51, and is configured to support the at least one depressed area 1 of the bone fracture, together with the pulling lug 51. In some embodiments, the support forms the same plane together with the pulling lug 51. In some embodiments, the end of the pulling lug 51 is a free end.

Regarding the apparatus 10e for the closed reduction of the bone fracture according to the fifth embodiment, the contact area between the depressed fracture 1 and the pulling lug 51 may be more widened due to the support 55, as compared to the above-embodiments.

As described above, any one of the apparatuses 10a, 10b, 10c, 10d, and 10e for the closed reduction of a bone fracture according to the first to fifth embodiments, which have the pulling lugs 51 in various shapes, is selected depending on the size of the fracture 1 to be operated and the size and the position of the incision 3, and inserted through the incision 3 of the fracture 1 to pull the fracture 1, thereby performing the operation of recovering the fracture 1.

Meanwhile, the apparatus for the closed reduction of the bone fracture according to the inventive concept may further include a hand piece 61, which is configured to be gripped by an operator, to support the apparatuses 10a, 10b, 10c, 10d, and 10e for the closed reduction of the bone fracture according to the first embodiment to the fifth embodiment described above.

Figure 6:
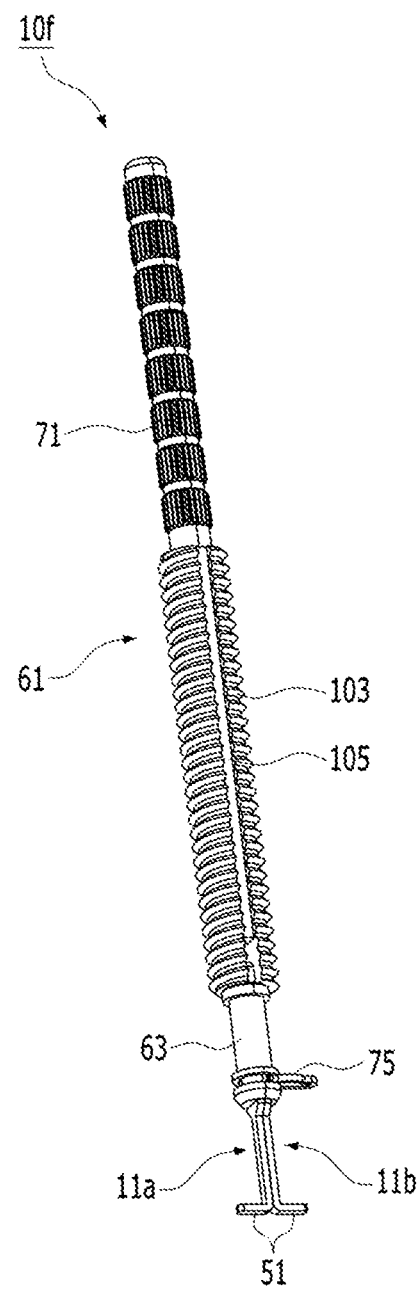
FIG. 6 is a view illustrating an apparatus for a closed reduction of a bone fracture, according to a sixth embodiment.
Figure 7:
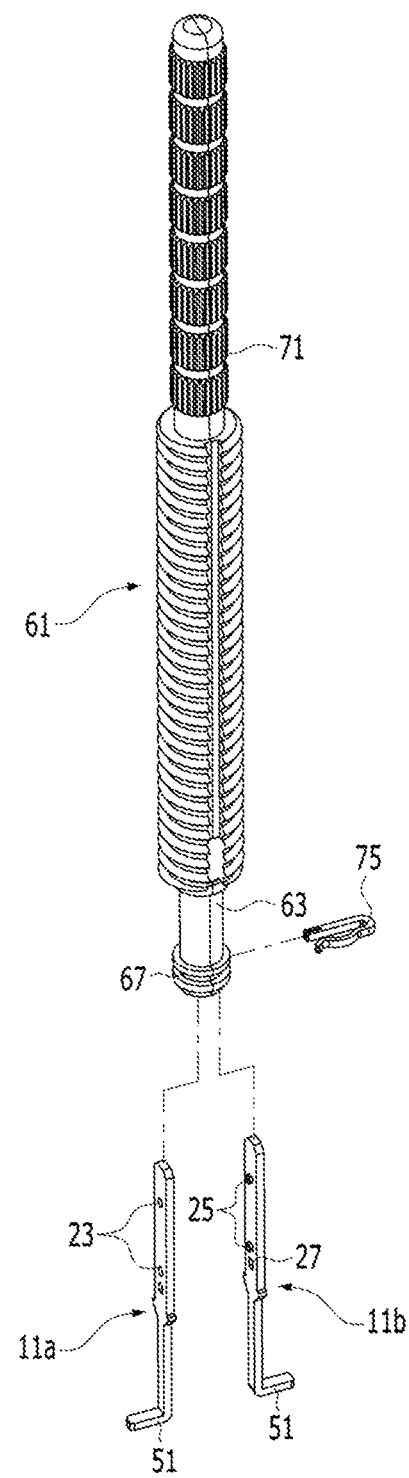
FIG. 7 is an exploded perspective view of FIG. 6.

FIGS. 6 and 7 illustrate an apparatus for the closed reduction of a bone fracture, according to a sixth embodiment.

The apparatus 10f for the closed reduction of the bone fracture according to the sixth embodiment includes the apparatus 10a for the closed reduction of the bone fracture according to the first embodiment and the apparatus 10b for the closed reduction of a bone fracture according to the second embodiment, which are described above, as a pair of pulling adaptors 11a and 11b.

In other words, each of the pair of pulling adaptors 11a and 11b includes the handle 21, the insertion rod 41, and the pulling lug 51. In the following description, for the convenience of explanation, the pulling adaptor positioned at the left side of FIG. 7 is referred to as a first pulling adaptor 11a and the pulling adaptor positioned at the right side of FIG. 7 is referred to as a second pulling adaptor 11b. The first pulling adaptor 11a has the same shape as the shape of the apparatus 10a for the closed reduction of a bone fracture according to the first embodiment and the second pulling adaptor 11b has the same shape as the shape of the apparatus 10b for the closed reduction of the bone fracture according to the second embodiment.

The handle 21 of each of the pulling adaptors 11a and 11b has the form of a bar having a predetermined length, the insertion rod 41 longitudinally extends from the handle 21, and the pulling lug 51 extends while being bent from the end of the insertion rod 41 perpendicularly to the insertion rod 41.

In addition, stoppers 43 are provided at the boundary area between the insertion rod 41 and the handle 21 along both edges of the insertion rod 41. The stoppers 43 protrude along both edges of the insertion rod 41 to be inclined with respect to an axis of the handle 21 toward the handle 21. Accordingly, the stoppers 43 restrict the pulling adaptors 11a and 11b from being moved toward the hand piece 61 when the pulling adaptors 11a and 11b are mounted on the hand piece 61.

Meanwhile, a pair of coupling holes 23 are formed through the handle 21 of the first pulling adaptor 11a, and a pair of coupling protrusions 25 are formed to protrude on the handle 21 of the second pulling adaptor 11b such that the pair of coupling protrusions 25 are coupled to the pair of coupling hole 23 of the first pulling adaptor 11a. Accordingly, the pulling lugs 51 of the first pulling adaptor 11a and the second pulling adaptor 11b protrude in opposite directions while making close contact with each other and coupled to each other by the coupling protrusions 25 and the coupling holes 23.

In addition, the handles 21 of the first pulling adaptor 11a and the second pulling adaptor 11b have pin holes 27 formed therethrough to be coupled to coupling pins to be described below.

The hand piece 61 has the shape of a rod having a circular sectional surface having a predetermined length.

The hand piece 61 has an insertion part 63 provided at one end thereof, in which the handles 21 of the pair of pulling adaptors 11a and 11b are inserted into the insertion part 63. The insertion part 63 has communication holes 67 to communicate with the pin holes 27 formed in the pair of pulling adaptors 11a and 11b.

The hand piece 61 has a grip part 71 provided at an opposite end thereof to grip the hand piece 61. The grip part 71 may be formed through a knurling process to prevent a hand of an operator gripping the grip part 71 from being slipped.

Components of a pulling part to be described below and interposed between the insertion part 63 of the hand piece 61 and the grip part 71 include a male screw part 103 having a male thread formed an outer circumferential surface of the hand piece 61 and a guide groove 105 formed at a predetermined depth in the male screw part 103 in the lengthwise direction of the hand piece 61. Although the male screw part 103 and the guide groove 105 are illustrated according to the present embodiment, the male screw part 103 and the guide groove 105 may be selectively provided if necessary.

In addition, according to the sixth embodiment, the apparatus 10f for the closed reduction of the bone fracture according to the sixth embodiment further includes the coupling pin 75.

The coupling pin 75 is coupled to the pin holes 27 of the pair of pulling adaptors 11a and 11b inserted into the insertion part 63 of the hand piece 61 and the communication hole 68 of the hand piece 61, so the pair of pulling adaptors 11 and 11b are fixed to the hand piece 61.

Accordingly, the apparatus 10f for the closed reduction of the bone fracture according to the sixth embodiment substantially has the form that the pulling lugs 51 of the first pulling adaptor 11a and the second pulling adaptor 11b protrude in opposite directions and are coupled to the hand piece 61.

In this case, although it is illustrated that the apparatus 10a for the closed reduction of the bone fracture according to the first embodiment and the apparatus 10b for the closed reduction of a bone fracture according to the second embodiment serve as the pair of pulling adaptors 11a and 11b mounted on the apparatus 10f for the closed reduction of the bone fracture according to the sixth embodiment, the inventive concept is not limited thereto. For example, at least one of apparatuses 10c, 10d, and 10e for the closed reduction of the bone fracture according to the third embodiment to the fifth embodiment described above may be provided as the pair of pulling adaptors 11a and 11b.

Figure 8:
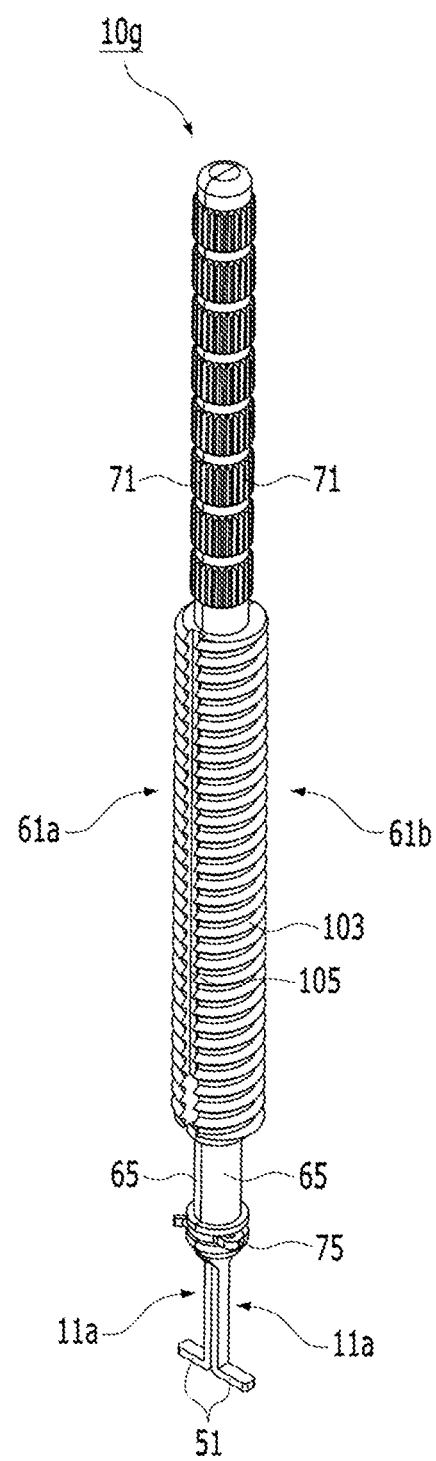
FIG. 8 is a view illustrating an apparatus for a closed reduction of a bone fracture, according to a seventh embodiment.
Figure 9:
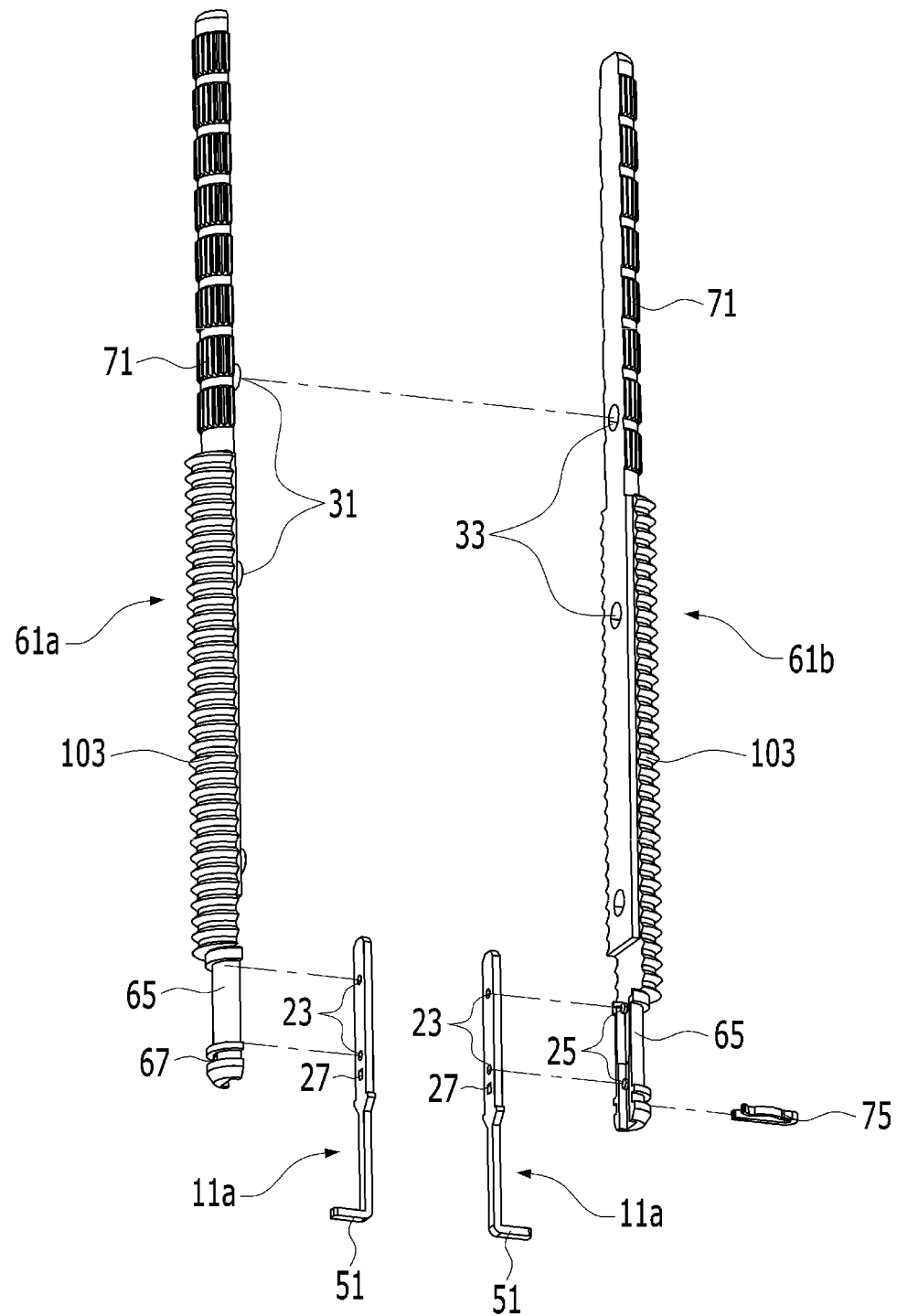
FIG. 9 is an exploded perspective view of FIG. 8.
Figure 10:
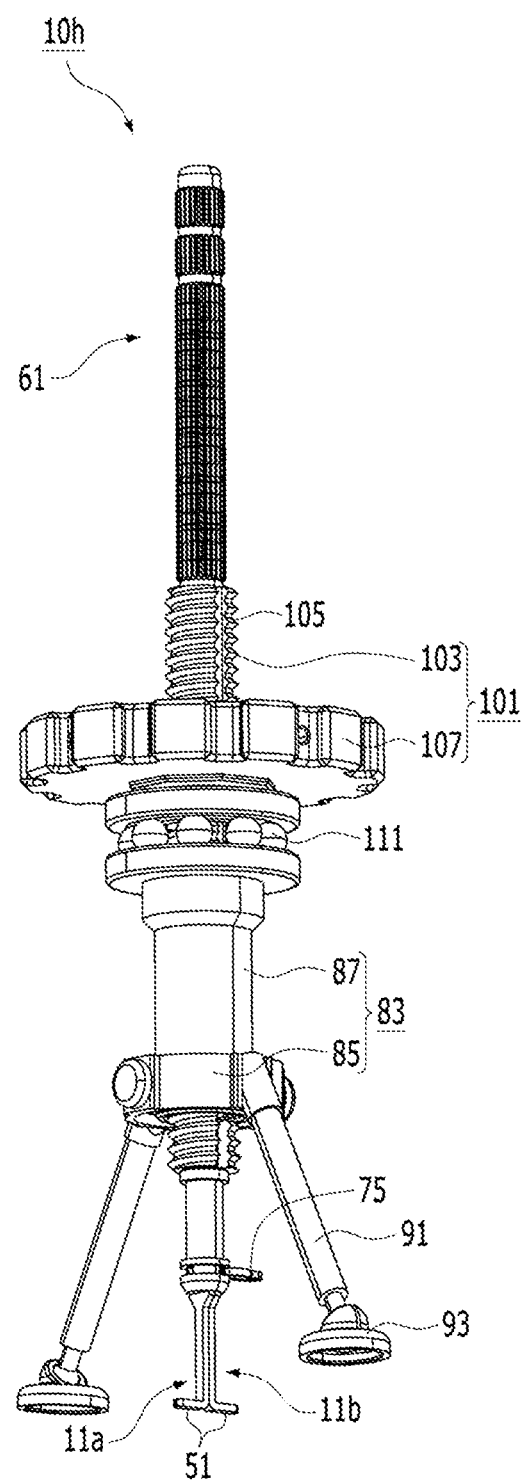
FIG. 10 is a view illustrating an apparatus for a closed reduction of a bone fracture, according to an eighth embodiment.
Figure 11:
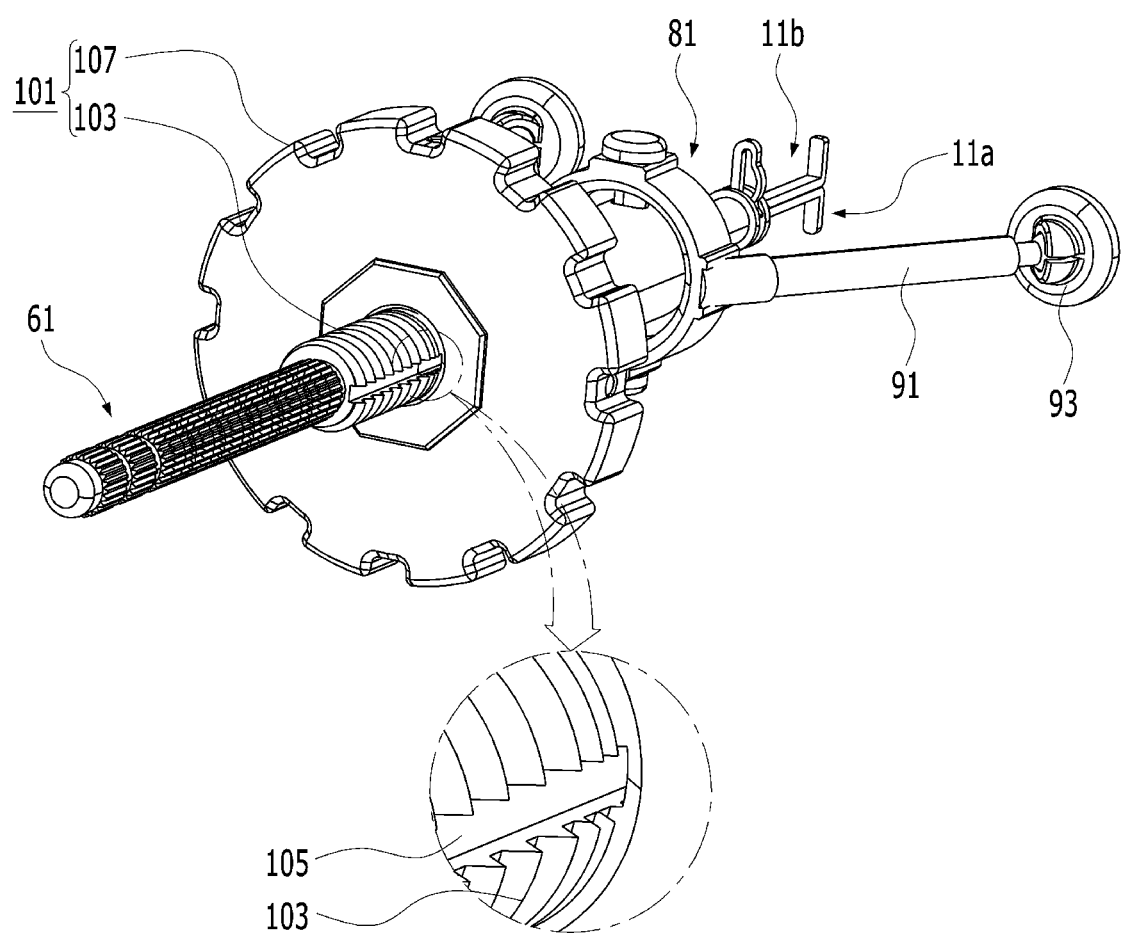
FIG. 11 is a perspective view of FIG. 10.
Figure 12:
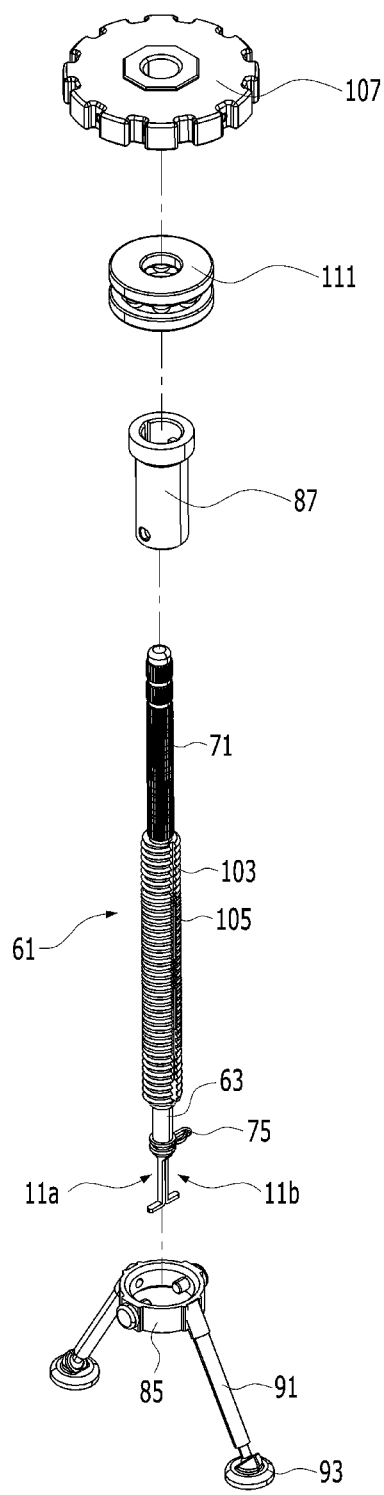
FIG. 12 is an exploded perspective view of FIG. 10.

FIGS. 8 and 9 illustrate an apparatus for the closed reduction of a bone fracture, according to a seventh embodiment.

As illustrated in drawings, an apparatus 10g for the closed reduction of a bone fracture according to a seventh embodiment has a structure that a pair of pulling adaptors 11a are mounted on a first half hand piece 61 and a second half hand piece 61b which are separately coupled to each other.

As the pair of pulling adaptor 11a mounted on the apparatus 10b for the closed reduction of the bone fracture according to the seventh embodiment, the apparatus 10a for the closed reduction of the bone fracture according to the first embodiment described above is provided.

The pair of pulling adaptors 11a include a handle 21, an insertion rod 41, and a pulling lug 51, as described in the apparatus 10a for the closed reduction of the bone fracture according to the first embodiment.

In addition, the handles 21 of the pulling adaptors 11a has coupling holes 23 formed therethrough to be coupled to a detaching part 65 of the first half hand piece 61a and a detaching part 65 of the second half hand piece 61b, which are different from the sixth embodiment described above.

Meanwhile, the hand piece of the apparatus 10b for the closed reduction of the bone fracture according to the seventh embodiment includes a first half hand piece 61a and a second half hand piece 61b provided separately in a lengthwise direction of the hand piece.

The first half hand piece 61a and the second half hand piece 61b may have a semi-spherical sectional surface form.

The detachable part 65 is provided at one end portion of each of the first half hand piece 61a and the second half hand piece 61b such that the handle 21 of the pulling adaptor 11a is detachable from the detachable part 65. The detachable part 65 has the communication hole 67 to communicate with the pin hole 27 formed in each pulling adaptor 11a. In addition, the detachable part 65 has coupling protrusions 25 protruding corresponding to the coupling holes 23 formed in each handle 21 of each pulling adaptor 11*a*. Accordingly, the pair of pulling adaptors 11*a* are coupled to the detachable parts 65 of the first half hand piece 61*a* and the second half hand piece 61*b*.

Each of the first half hand piece 61*a* and the second half hand piece 61*b* has a grip part 71 provided at an opposite end portion thereof to grip the hand pieces 61*a* and 61*b*. The grip part 71 may be formed through a knurling process to prevent a hand of an operator gripping the grip part 71 from being slipped.

The first half hand piece 61*a* has a plurality of fitting protrusions 31 protruding toward the second half hand piece 61*b*, and the second half hand piece 61*b* has a plurality of fitting grooves 33 recessed therein such that the plurality of fitting protrusions 31 are fitted into the plurality of fitting grooves 33. As the first half hand piece 61*a* is half coupled to the second half hand piece 61*b*, the first half hand piece 61*a* and the second half hand piece 61*b* have the form of a rod having a circular sectional surface, that is, have one hand piece form.

In addition, each of the first half hand piece 61*a* and the second half hand piece 61*a* is provided, between the insertion part 63 and the grip part 71 thereof, with a male screw part 103, which is provided on an outer circumferential surface thereof with a male thread, and a guide groove 105 which is recessed at a predetermined depth in the male screw part 103 in a lengthwise direction of each of the first half hand piece 61*a* and the second half hand piece 61*a*, in which the male screw part 103 and the guide groove 105 serve as components of a pulling part to be described below. Although the male screw part 103 and the guide groove 105 are illustrated according to the present embodiment, the male screw part 103 and the guide groove 105 may be selectively provided if necessary.

In addition, according to the seventh embodiment, an apparatus 10*g* for the closed reduction of the bone fracture further include a coupling pin 75.

As the coupling pin 75 is engaged with the communication hole 67 of each of the first half hand piece 61*a* and the second half hand piece 61*b* and the pin hole 27 of each of the pulling adaptors 11*a* mounted in detachable parts 65 of the first half hand piece 61*a* and the second half hand piece 61*b*, the pair of pulling adaptors 11*a* are fixed to the first half hand piece 61*a* and the second half hand piece 61*b*.

Therefore, the apparatus 10*b* for the closed reduction of the bone fracture according to the seventh embodiment has the form that the pulling lugs 51 of the pair of pulling adaptors 11*a* are coupled to the hand piece while protruding in opposite directions.

In this case, although it is illustrated that apparatuses 10*a* for the closed reduction of the bone fracture according to the first embodiment are provided as the pair of pulling adaptors 11*a* mounted on the apparatus 10*g* for the closed reduction of the bone fracture according to the seventh embodiment, the inventive concept is not limited thereto. For example, at least one of apparatuses 10*b*, 10*c*, 10*d*, and 10*e* for the closed reduction of the bone fracture according to the second embodiment to the fifth embodiment described above may be provided.

As described above, when the apparatus 10*f* for the closed reduction of the bone fracture according to the sixth embodiment and the apparatus 10*g* for the closed reduction of the bone fracture according to the seventh embodiment are inserted into the incision 3 of the depressed fracture 1 to pull the depressed fracture 1, the force generated in a horizontal direction in the apparatuses 10*f* and 10*g* is canceled by the interaction between the pair of pulling adaptors 11*a* and 11*b*, for example, between the insertion rods 41 of the pair of pulling adaptors 11*a* and 11*b*, and only the force generated in the vertical direction acts to the apparatuses 10*f* and 10*g* for the closed reduction of the bone fracture to easily pull the depressed fracture 1 to recover the depressed fracture 1.

In addition, the apparatus 10*f* for the closed reduction of the bone fracture according to the sixth embodiment and the apparatus 10*g* for the closed reduction of the bone fracture according to the seventh embodiment may selectively mount, thereon, pulling adaptors having various shapes depending on the shape of a part to be operated and the size of the incision 3 for use.

FIGS. 10 to 13 are views illustrating an apparatus for the closed reduction of a bone fracture, according to an eighth embodiment.

As illustrated in drawings, according to the eighth embodiment, the apparatus 10*h* for the closed reduction of the bone fracture further includes a mounting member 81, which is different from the sixth embodiment.

The mounting member 81 includes a pivot joint 83 and a plurality of legs 91.

Figure 13:
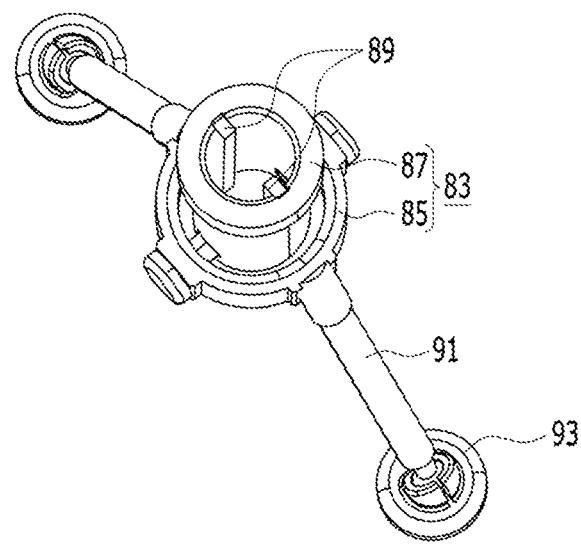
FIG. 13 is a perspective view of a pivot joint of FIG. 10.

The pivot joint 83 includes a joint body 85 and a sleeve 87 pivotably coupled to the joint body 85 as illustrated in FIG. 13.

The sleeve 87 has the form of a hollowed pipe having a circular section surface, and the hand piece 61 is pivotably supported to the sleeve 87 such that the hand piece 61 is linearly movable. In addition, the sleeve 87 is provided on the inner circumference thereof with a pair of guide protrusions 89 which protrude to a predetermined height in an insertion direction of the hand piece 61, for example, in the lengthwise direction of the sleeve 87. The pair of guide protrusions 89 are formed on the inner circumference of the sleeve 87 in such a manner that the guide protrusions 89 are symmetrical to each other.

The plurality of legs 91 are provided at an outer portion of the pivot joint 83 to support the pivot joint 83 while spacing the pivot joint 83 from the fracture 1.

In addition, the plurality of legs 91 are rotatably hinged to the pivot joint 83. Accordingly, the apparatus 10*h* for the closed reduction of the bone fracture may be stably mounted on various parts that need to be operated, even if such various parts have linear shapes, are recessed, or have the shape of a curve protruding.

The end of each leg 91 has a pad 93 mounted thereon and formed of a rubber or a silicon material to be elastically supported around the fracture 1.

In addition, according to the eighth embodiment, the apparatus 10*h* for the closed reduction of the bone fracture further includes a pulling part 101 to pull the hand piece 61 pivotably supported to the mounting member 81.

The pulling part 101 includes a male screw part 103 and a knob 107.

The male screw part 103 is formed on one area of an outer circumference of the hand piece 61. In other words, the male screw part 103 is formed on an outer circumference of the hand piece 61 passing through the pivot joint 83. In addition, the male screw part 103 has a pair of guide grooves 105 recessed at a predetermined depth in the lengthwise direction of the hand piece 61 corresponding to the pair of guide protrusions 89 of the pivot joint 83. The guide protrusions 89 of the pivot joint 83 are movably fitted into the guide groove 105 of the hand piece 61.

The knob 107 is screwed with the male screw part 103 to be slidable with respect to the pivot joint 83. The knob 107 is formed in the inner circumference thereof with a thread having the same specifications as those of the male screw part 103.

A bearing 111 is interposed between the knob 107 and the sleeve 87 to support the knob 107 rotatably with respect to the sleeve 87.

Accordingly, the knob 107 moves the hand piece 61 up from the fracture 1 through a screw motion with the male screw part 103.

In other words, when the knob 107 is rotated in one direction while sliding with respect to the pivot joint 83, the hand piece 61 having the male screw part 103 is moved up. To the contrary, when the knob 107 is rotated in an opposite direction while sliding with respect to the pivot joint 83, the hand piece 61 having the male screw part 103 is moved down.

Meanwhile, when the knob 107 is rotated in the one direction or the opposite direction, the guide protrusion 89 of the pivot joint 83 is movably fitted into the guide groove 105 of the hand piece 61. The guide protrusion 89 is protruded at a predetermined height from an inner circumference of the pivot joint. Accordingly, as the knob 107 is rotated, the hand piece 61 is not rotated with respect to the pivot joint 83 and performs a linear movement while being moved up.

Figure 14:
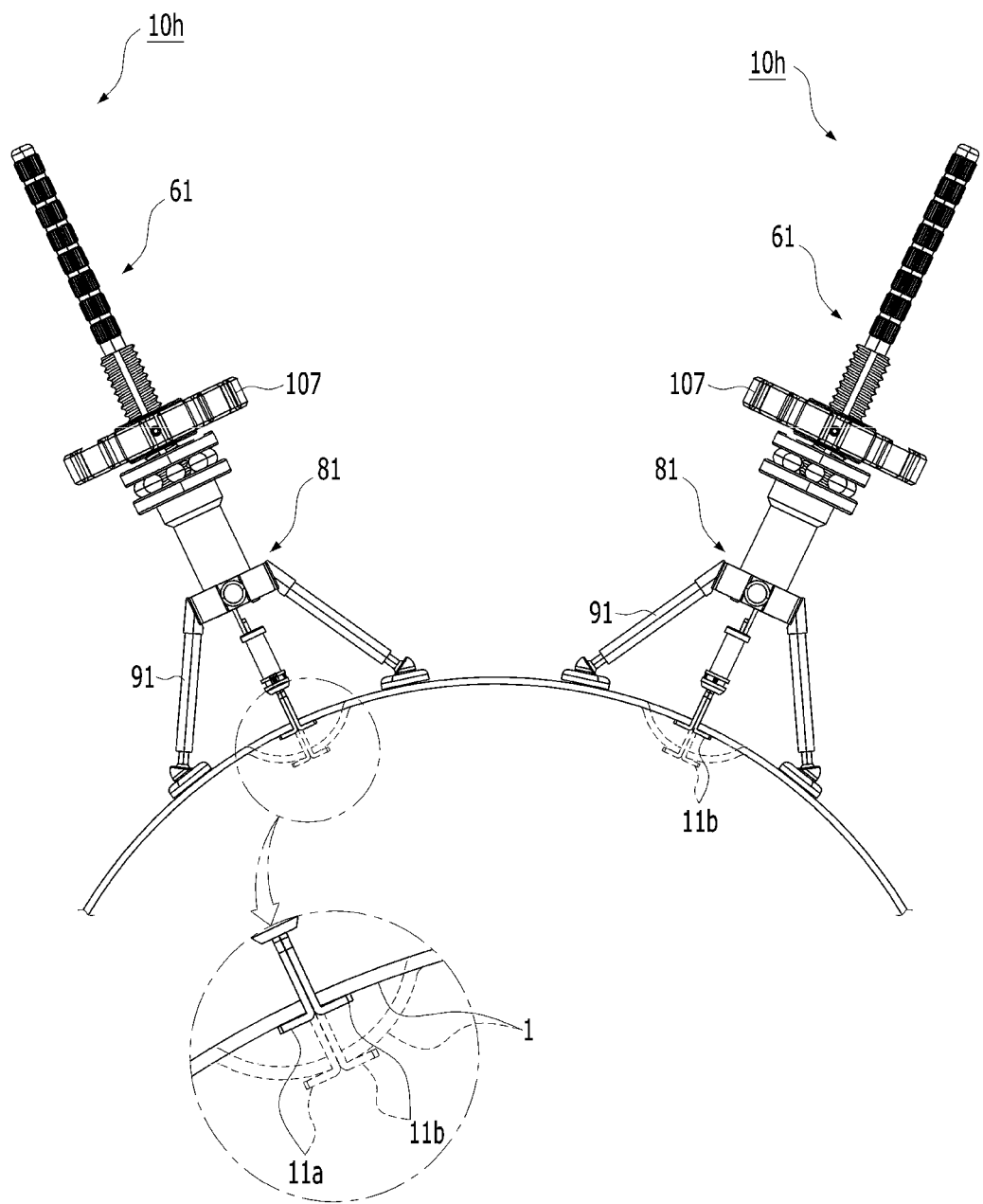
FIG. 14 is a view illustrating that the apparatus for the closed reduction of the bone fracture according to the eighth embodiment is mounted on the fracture.

FIG. 14 is a view illustrating that the apparatus 10h for the closed reduction of the bone fracture according to the eighth embodiment is mounted on the fracture 1 having a curved shape.

Figure 15:
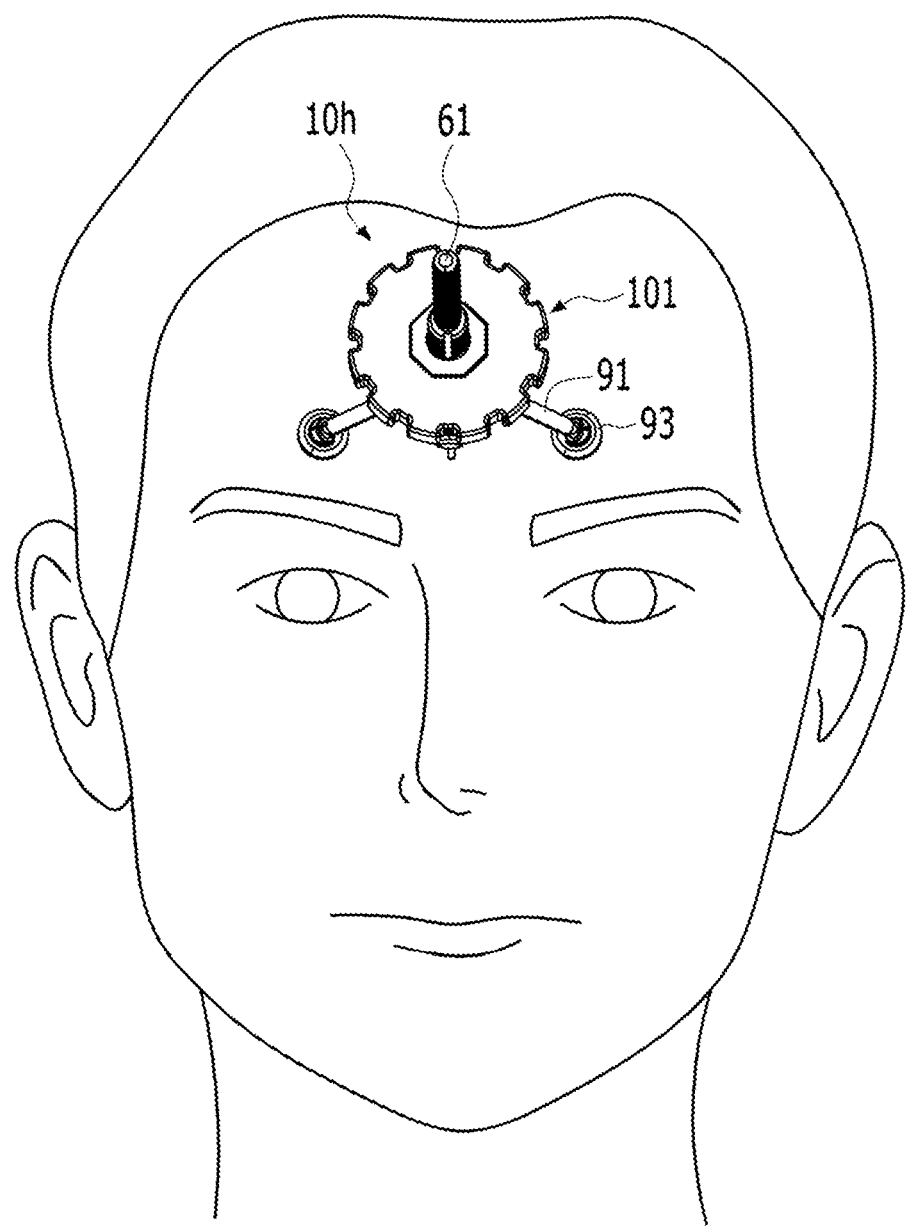
FIG. 15 is a view illustrating that an apparatus for the closed reduction of the bone fracture according to the eighth embodiment is mounted on a facial surface.

In addition, FIG. 15 is a view illustrating that the apparatus 10h for the closed reduction of the bone fracture according to the eighth embodiment is mounted on a facial surface.

FIGS. 16A to 16E illustrate the operation procedure using the apparatus 10h for the closed reduction of the bone fracture according to the eighth embodiment.

Figure 16A:
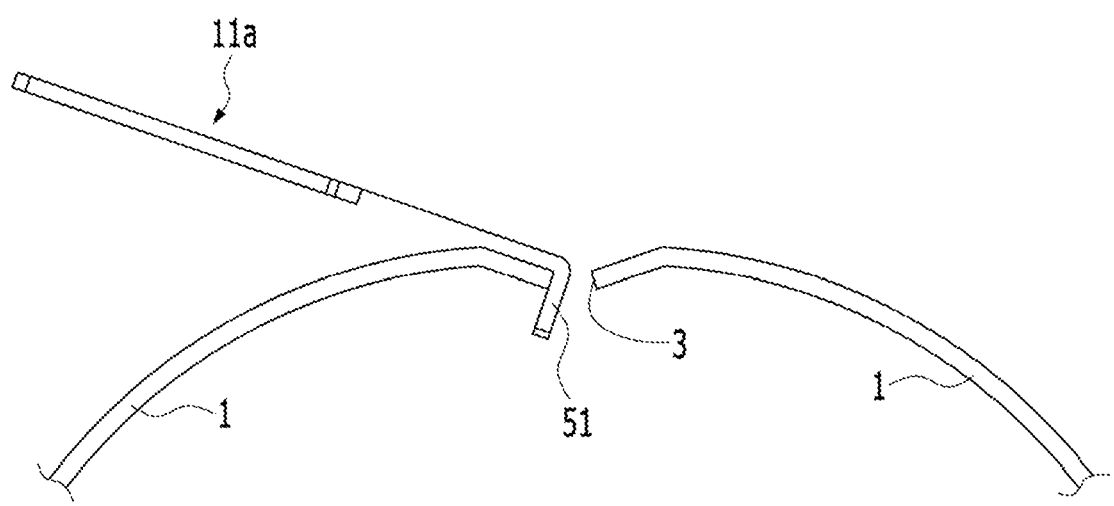
FIGS. 16A to 16E are views illustrating an operation procedure using the apparatus for the closed reduction of the bone fracture according to the eighth embodiment.
Figure 16B:
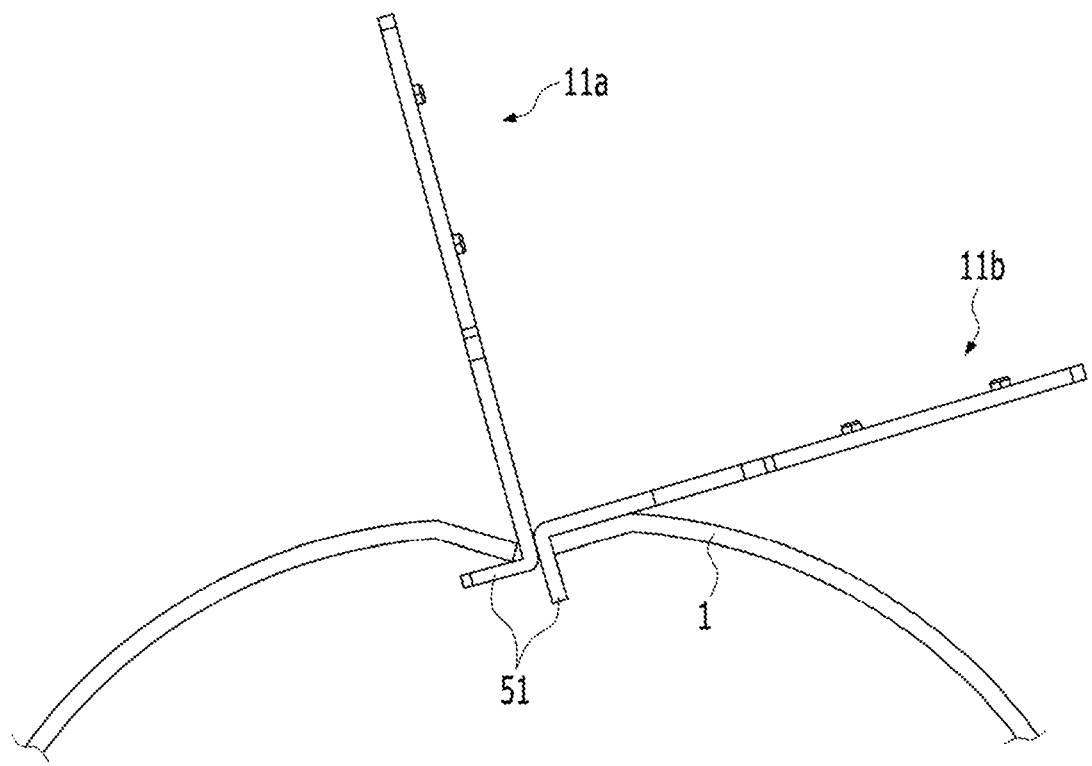

Hereinafter, the operation procedure will be described with reference to the above drawings. As illustrated in FIGS. 16A and 16B, the pair of pulling adaptors 11a and 11b are inserted into the fracture 1 such that the pulling lugs of the pulling adaptors 11a and 11b are inserted into the fracture 1 through the incision 3 of the fracture 1.

Figure 16C:
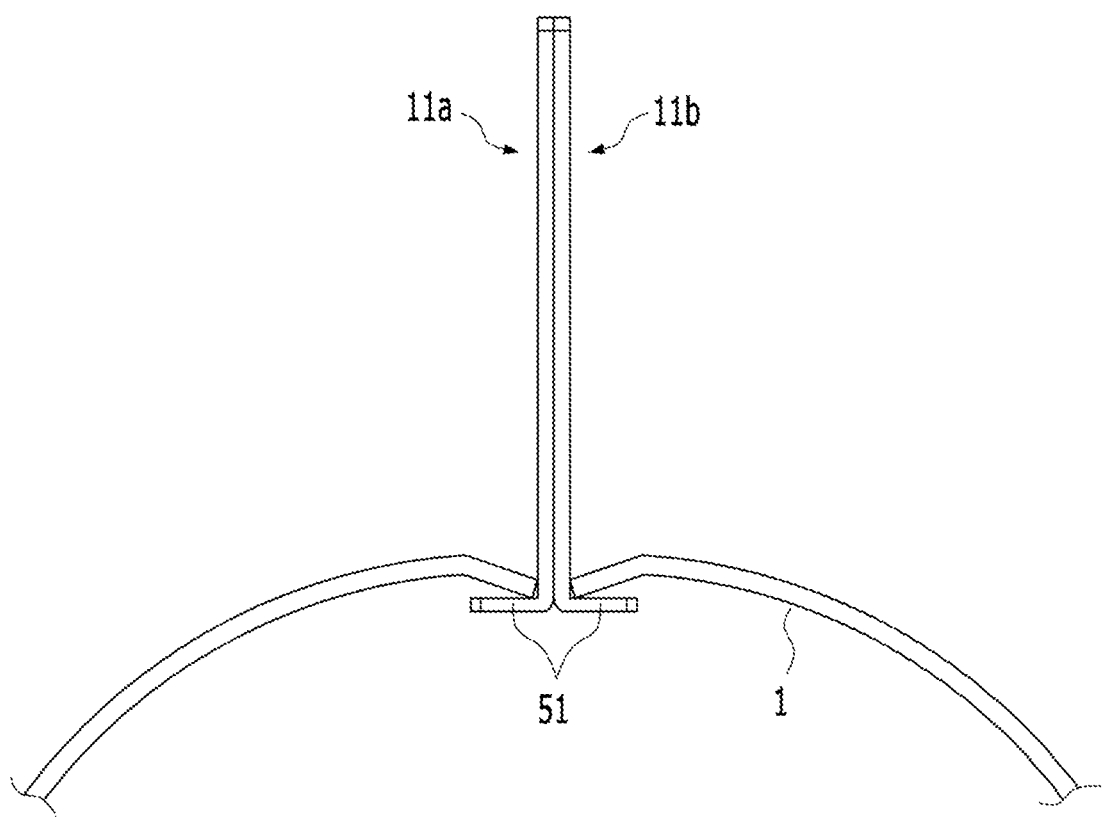

Thereafter, as illustrated in FIG. 16C, the pair of pulling adaptors 11a and 11b are fitted into each other by the coupling protrusion 25 and the coupling groove 13 such that the pulling lugs 51 of the pair of pulling adaptors 11a and 11b protrude in opposite directions and are disposed vertically to the incision 3.

Figure 16D:
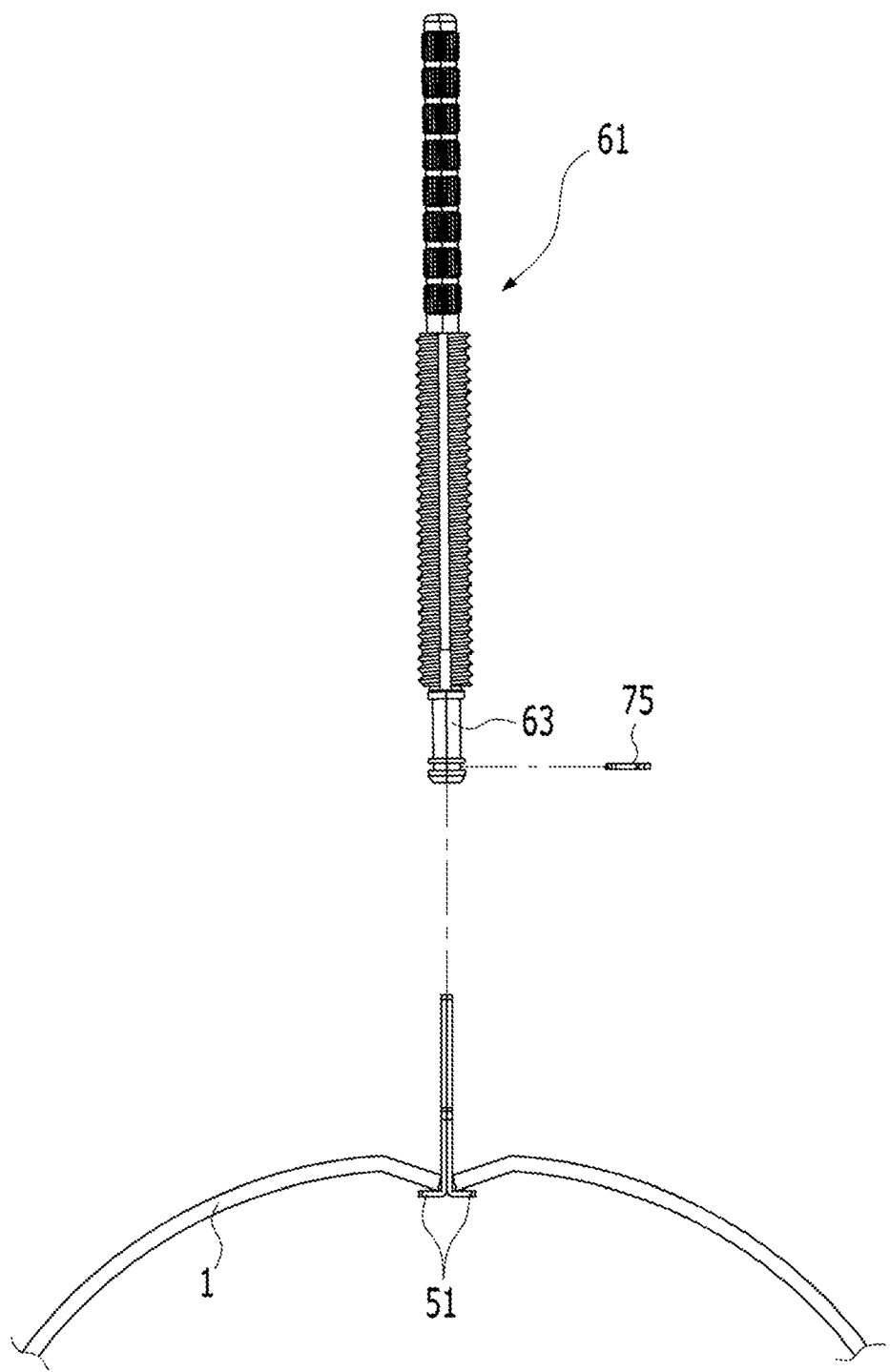

In addition, as illustrated in FIG. 16D, the hand piece 61 is disposed above the pair of pulling adaptors 11a and 11b and the handles 21 of the pair of pulling adaptors 11a and 11b are inserted into the insertion part 63 of the hand piece 61. Then, the pair of pulling adaptors 11a and 11b are fixed to the hand piece 61 through the coupling pin 75.

Figure 16E:
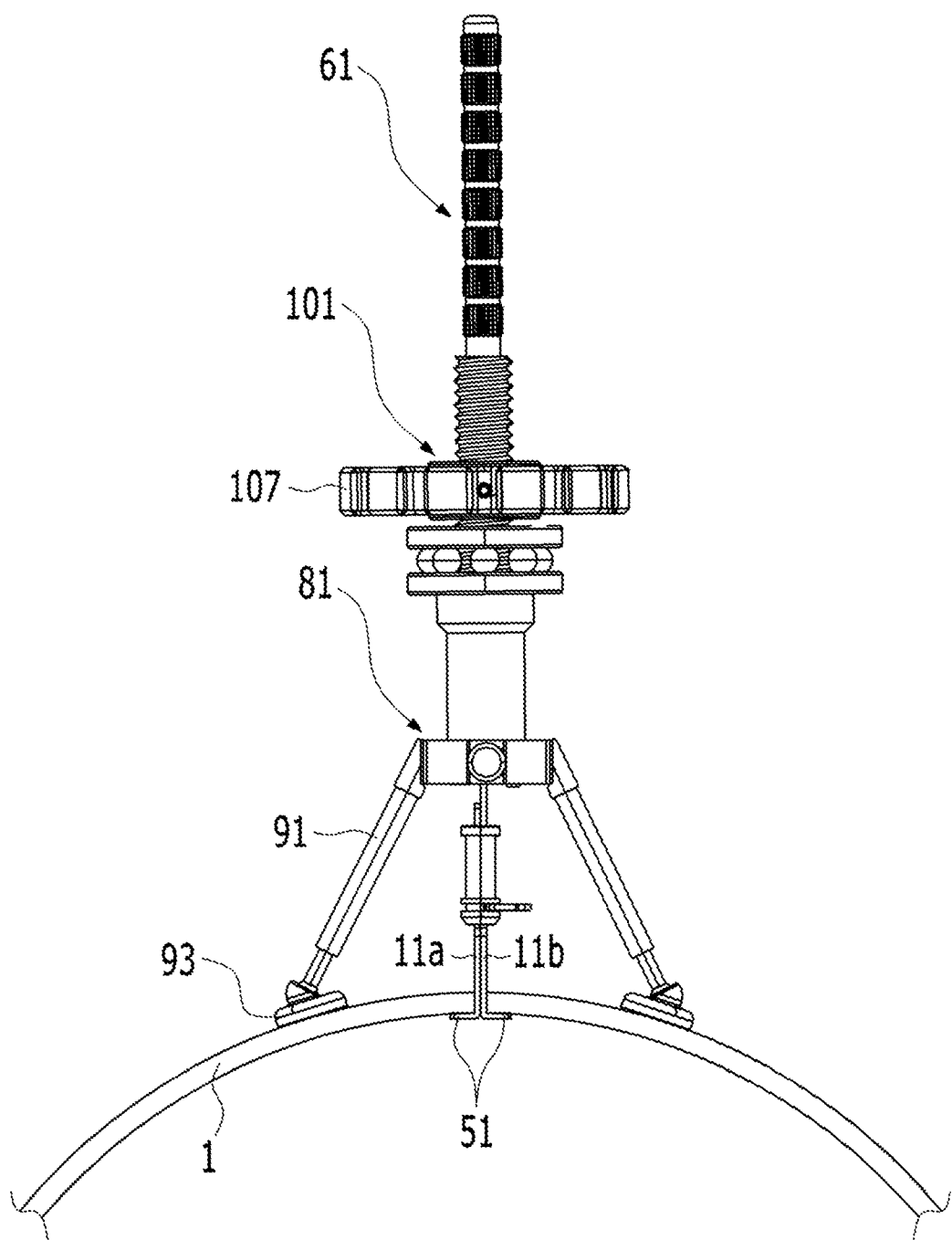

Thereafter, as illustrated in FIG. 16E, the mounting member 81 and the pulling part 11 are mounted on the hand piece 61. In this case, each leg 91 of the mounting member 81 is supported around the fracture 1.

In the state that the hand piece 61 is supported to the pivot joint 83, the knob 107 is screwed with the male screw part 103 of the hand piece 61.

In addition, as the knob 107 is rotated in one direction while sliding with respect to the pivot joint 83, the hand piece 61 having the male screw part 103 is moved up from the fracture 1.

As the knob 107 is rotated, the hand piece 61 is moved up. For example, as the pulling lug 51 of each of the pulling adaptors 11a and 11b is moved up to support the depressed fracture 1 while pulling the depressed fracture 1.

In this case, the hand piece 61 is stably supported by the mounting member 81, so the fluctuation of the hand piece 61 is minimized when the operator pulls the fracture 1, thereby stably recovering the fracture 1. In addition, as the lifting of each pulling lug 51 mounted on the hand piece 61 is finely adjusted by the pulling part 101, the depressed fracture 1 is pulled while being precisely and finely adjusted and thus recovered.

When the pulling work of the depressed fracture 1 is complemented, after the mounting member 81 is removed from the surrounding of the fracture 1 in the reverse order, the pulling adaptors 11a and 11b mounted on the hand piece 61 are withdrawn out of the fracture 1 through the incision 3, so the hand piece 61 is separated from the operator. Accordingly, the recovery operation of the depressed fracture 1 is completed.

Meanwhile, the apparatus 10h for the closed reduction of a bone fracture according to the eighth embodiments may be used without the component of the pulling part 101.

The pulling lugs 51 of the pair of pulling adaptors 11a and 11b are inserted through the incision 3 of the fracture 1 and then the handles 21 of the pulling adaptors 11a and 11b are inserted into the insertion part 63 while the pair of pulling adaptors 11a and 11b are fixed to the hand piece 61. Thereafter, the mounting member 81 is mounted on the hand piece 61. In this case, each leg 91 of the mounting member 81 is supported around the fracture 1.

In the state that the hand piece 61 is supported to the pivot joint 83, the depressed fracture 1 is supported and pulled using the pulling lugs 51 mounted on the hand piece 61 to space the hand piece 61 from the fracture 1. In this case, the hand piece 61 is stably mounted by the mounting member 81. In addition, the hand piece 61 is mounted at various parts and used by changing the pulling direction. When the operator pulls the fracture 1, the fluctuation of the hand piece 61 may be minimized, so the fracture 1 is stably recovered.

In this case, when the incision 3 is not formed in the fracture 1, the incision 3 is formed in the fracture 1 using a drill (not illustrated). Then, the apparatus for the closed reduction of the bone fracture, which has the insertion rod and the pulling lug corresponding to the diameter of the incision 3, is inserted through the incision 3, so the recovery operation of pulling the fracture 1 may be performed.

As described above, according to the inventive concept, the pulling lug is provided at the end of the insertion rod inserted into the depressed fracture 1, in which the pulling lug extends while being bent perpendicularly to the insertion rod or inclined with respect to the insertion rod. Accordingly, the insertion and removal are easily performed through the smaller incision. In addition, the depressed fracture is stably pulled and recovered regardless with the skin thickness.

In addition, as the hand piece to which the pulling adaptors are supported may be mounted on the mounting member and pulled, the apparatus for the closed reduction of the bone fracture may be mounted at various parts and used while changing the pulling direction. When the operator pulls the fracture, the fluctuation of the pulling adaptor and the hand piece are minimized, thereby stably recovering the fracture.

In addition, the pulling part 101 pivotably supported to the mounting member to pull the hand piece, so the depressed fracture 1 is pulled while being precisely and finely adjusted, to be recovered.

Meanwhile, according to the embodiments described above, although it is illustrated that the stopper is provided the apparatus for the closed reduction of the bone fracture, the stopper may be selectively provided.

In addition, the pulling lugs of the apparatuses for the closed reduction of the bone fracture according to the first embodiment and the second embodiment may include at least one of the anti-slip protrusions illustrated according to the fourth embodiment described above and the support illustrated according to the fifth embodiment.

According to the inventive concept, the pulling lug, which extends while being bent perpendicularly to the insertion rod or inclined with respect to the insertion rod, is provided at the free end of the insertion rod inserted into the depressed fracture and the fracture is pulled using the pulling lug. Accordingly, the apparatus may easily perform insertion and removal through the smaller incision, and the depressed fracture is stably pulled and recovered regardless of the skin thickness.

In addition, the hand piece supported by the pulling adaptor is mounted on the mounting member to perform a pulling operation. Accordingly, the apparatus for the closed reduction of the bone fracture may be mounted at various parts and used by changing the pulling directions. When the operator pulls the fracture, the fluctuation of the pulling adaptor and the hand piece may be minimized and the fracture may be stably recovered.

In addition, the pulling part to pull the hand piece pivotably supported to the mounting member is provided, so the depressed fracture is pulled while being precisely and finely adjusted and thus recovered.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. An apparatus for closed reduction of a bone fracture, the apparatus comprising:
   a pulling adaptor including:
   a handle configured to be gripped by an operator;
   an insertion rod that is extended from the handle in a longitudinal direction of the handle, and configured to be inserted into the bone fracture which is depressed in at least one area thereof;
   a pulling lug that is bent and extended from an end of the insertion rod such that a longitudinal direction of the pulling lug is perpendicular to a longitudinal direction of the insertion rod or such that the pulling lug is inclined with respect to the insertion rod, the pulling lug being configured to be inserted into the at least one depressed area of the bone fracture, in order to pull the bone fracture; and
   a pair of anti-slip protrusions, each of the pair of anti-slip protrusions has a semi-spherical sectional surface form, protrude from an upper surface of the pulling lug, and is configured to prevent the bone fracture from being slipped over the pulling lug.

2. The apparatus of claim 1, further comprising:
   a slot that penetrates a portion of the insertion rod and a portion of the pulling lug;
   a pair of coupling holes; and
   a pin hole,
   wherein the slot is configured to be inserted by a portion of an insertion rod and a portion of a lug of another apparatus,
   wherein the pair of coupling holes is configured to be coupled with a pair of coupling protrusions of the another apparatus, and
   wherein the pin hole is configured to be coupled with a pin of the another apparatus.

3. The apparatus of claim 1, further comprising:
   a pair of stoppers that are positioned at a boundary area between the insertion rod and the handle, and protrude along both edges of the insertion rod to be inclined with respect to an axis of the handle toward the handle.

4. An apparatus for closed reduction of a bone fracture, the apparatus comprising:
   a pulling adaptor including:
   a handle configured to be gripped by an operator;
   an insertion rod that is extended from the handle in a longitudinal direction of the handle, and configured to be inserted into the bone fracture which is depressed in at least one area thereof;
   a pulling lug that is bent and extended from an end of the insertion rod such that a longitudinal direction of the pulling lug is perpendicular to a longitudinal direction of the insertion rod or such that the pulling lug is inclined with respect to the insertion rod, the pulling lug being configured to be inserted into the at least one depressed area of the bone fracture, in order to pull the bone fracture;
   a support that is extended to be protruded from an end portion of the pulling lug, is configured to support the at least one depressed area of the bone fracture, together with the pulling lug, forms the same plane together with the pulling lug having an end portion that is a free end, and is positioned along a periphery of the free end of the pulling lug;
   a slot that penetrates a portion of the insertion rod and a portion of the pulling lug;
   a pair of coupling holes; and
   a pin hole,
   wherein the slot is configured to be inserted by a portion of an insertion rod and a portion of a lug of another apparatus,
   wherein the pair of coupling holes is configured to be coupled with a pair of coupling protrusions of the another apparatus, and
   wherein the pin hole is configured to be coupled with a pin of the another apparatus.

5. The apparatus of claim 4, further comprising:
   a pair of stoppers that are positioned at a boundary area between the insertion rod and the handle, and protrude along both edges of the insertion rod to be inclined with respect to an axis of the handle toward the handle.

* * * * *